United States Patent [19]

Gober

[11] Patent Number: 5,578,066
[45] Date of Patent: Nov. 26, 1996

[54] DEVICE TO DISCHARGE HABITUAL FINGER SUCKING

[76] Inventor: Giles D. Gober, 127 Sunset La., DeRidder, La. 70634

[21] Appl. No.: 520,743

[22] Filed: Aug. 29, 1995

[51] Int. Cl.⁶ .................................................. A61N 1/18
[52] U.S. Cl. ......................... 607/58; 607/115; 607/134; 128/880
[58] Field of Search ............................ 607/1, 2, 45, 58, 607/63, 75, 134, 115, 145, 150, 151, 153; 128/878–880

[56] References Cited

U.S. PATENT DOCUMENTS

| 230,194 | 7/1880 | Osselin et al. | 607/145 |
| 371,521 | 10/1887 | Rowell | 607/145 |
| 4,178,589 | 12/1979 | Nunn et al. | 128/880 |
| 4,692,748 | 9/1987 | Pinsak et al. | 128/880 |

FOREIGN PATENT DOCUMENTS

| 86/07543 | 12/1986 | Australia | 607/116 |
| 3222967 | 10/1991 | Japan | 607/1 |

Primary Examiner—William E. Kamm
Assistant Examiner—George R. Evanisko
Attorney, Agent, or Firm—Rodney Bryant Jordan

[57] ABSTRACT

An apparatus for discouraging habitual finger sucking by delivering a small current to an individual's tongue. An electrical current is delivered by two electrodes mounted within an adhesive band which is wrapped around the individual's finger and the adhesive band having contact points where the electrodes are exposed to the individual's tongue. The current may be produced by the band itself by constructing the band in layers including a layer supplying an electrolyte and a layer supplying two dis-similar metals, thus producing a current that can be delivered directly to the individual's tongue.

5 Claims, 6 Drawing Sheets

DEVICE TO DISCHARGE HABITUAL FINGER SUCKING

BACKGROUND OF THE INVENTION

The present invention relates to a device to be used in discouraging habitual thumb or finger sucking by individuals, especially during sleep. Thumb sucking, while harmless for the very young, can result in harmful physical and sociological effects if carried on into the later years of development. Individuals may be ridiculed by their peers, and deformities of the mouth and teeth may develop if the practice is continued. Although thumb sucking tends to end with the onslaught of ridicule from peers, there is the occasional individual who is unable to resist. There are also those individuals who continue to suck their thumb or fingers, quite involuntarily, in their sleep. It is this group of individuals that will benefit most from this invention.

DESCRIPTION OF THE PRIOR ART

Past attempts to resolve this problem have varied widely, with limited success. Various substances have been used for coating the individual's fingers so that the fingers will taste very bitter, hot or otherwise undesirable for the sucking. Usually the individual continues the attempt to suck the fingers until the substance becomes diluted and/or removed, thereby becoming ineffective. Physical and verbal punishment may be effective, if and only if the individual is aware of his or her actions, the actions are observed by the parents, and the individual is capable of understanding the meaning and intent of the punishment. These methods are obviously ineffective for individuals who nocturnally suck their fingers. The standard dental procedure for addressing this problem is the installation of a dental appliance. The dental appliance is an apparatus consisting of wires that is installed within the individual's mouth. The purpose of the appliance is to make it difficult for the individual to form a vacuum on the fingers, thereby relieving the satisfaction of sucking. These devices are very costly, uncomfortable, and beyond the realm of what most parents would like to see their children endure, especially in relation to a disorder that at first glance seems harmless.

SUMMARY OF THE INVENTION

The anti finger sucking device described herein consists of an apparatus that will generate a disagreeable taste and/or sensation in the mouth of the individual through the conduction of a very slight electrical current through the natural electrolyte present in the individual's saliva and tongue tissues. An adhesive band, constructed of non toxic substances, is wrapped around and thus fastened to the fingers being sucked by that individual. This band is equipped with two electrodes through which the current is passed. These electrodes may be connected through electrical leads to an external current supply such as a battery. The fact that batteries are relatively simple in construction and may be constructed of non toxic materials gives rise to the possibility of producing an adhesive strip which is itself a battery. Considering that a battery consists of electrodes that are constructed from dissimilar metals that have different electrode potentials that are in contact with an electrolyte, the strip could be powered by two electrodes having different electrode potentials in contact with the individual's natural electrolyte present in the saliva. This strip is constructed with non toxic materials, and in such a manner so that the electrodes will come in contact with the tongue when sucking occurs.

DETAILED DESCRIPTION OF THE INVENTION

Figure 1:
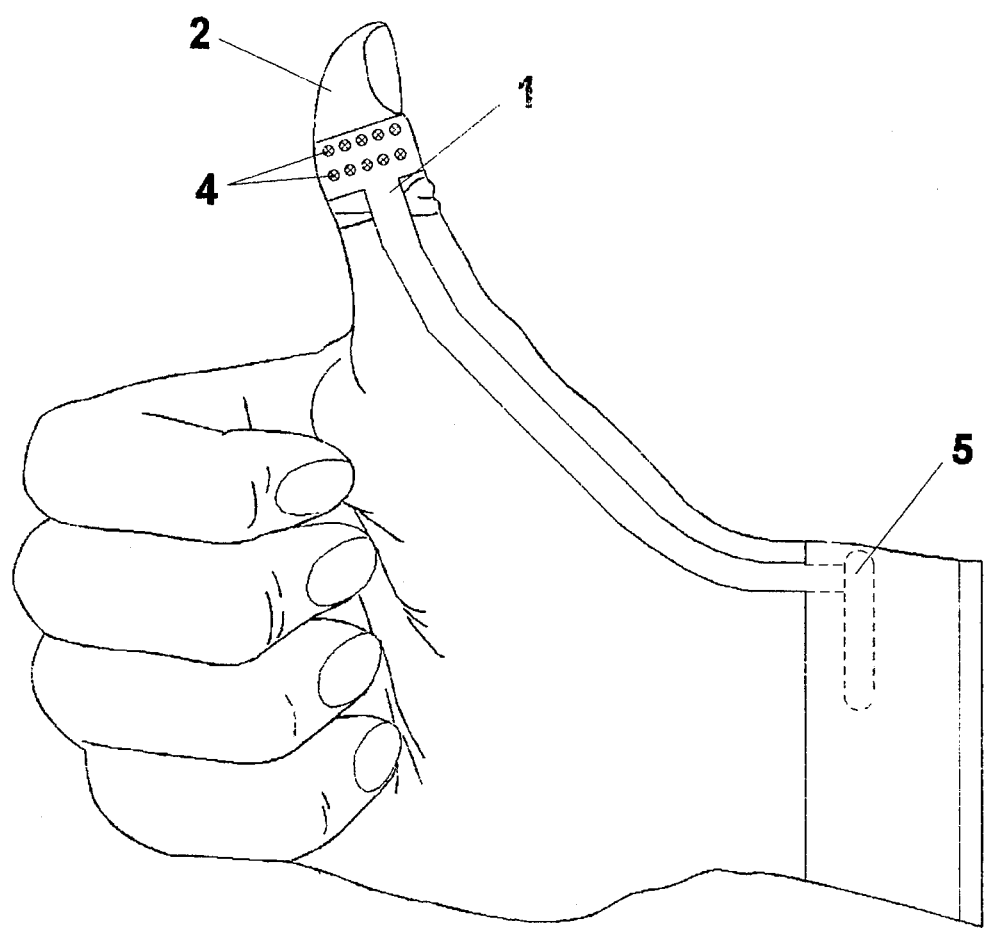
FIG. 1 is a view of the device attached to an individual's finger where the device employs an external voltage supply.
Figure 2:
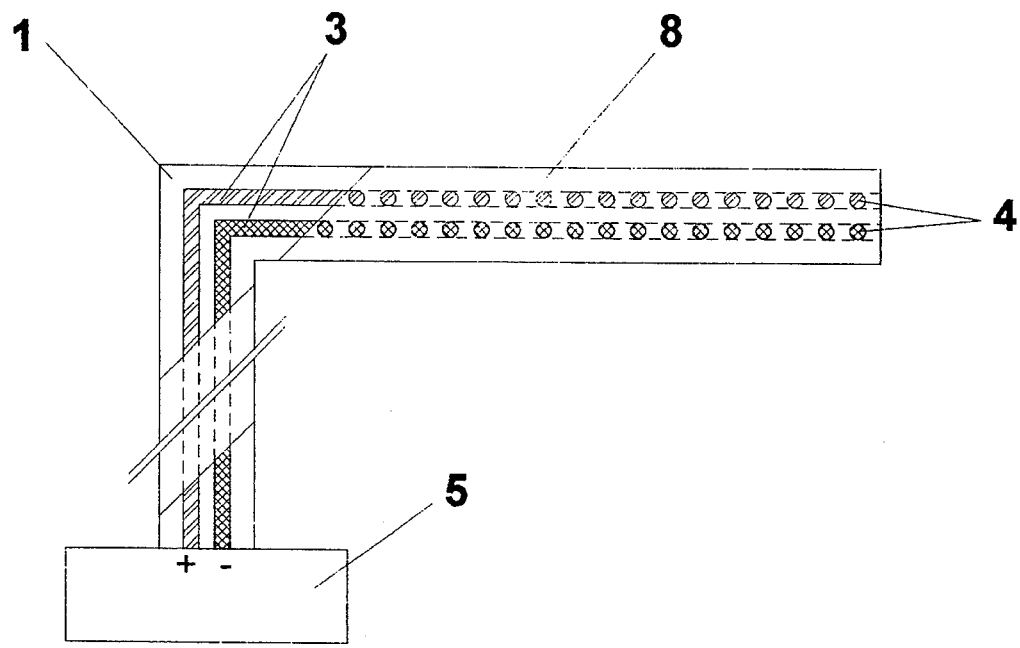
FIG. 2 is a front elevation view of the device where the device employs an external voltage supply.

Referring to the drawings, and more specifically to FIGS. 1 and 2, it can be seen that an adhesive band 1 is wrapped around an individual's finger 2. Electrodes 3 are fitted into the adhesive band 1 and covered with a perforated electrode mask 8 so that contact points 4 are un-insulated and facing away from the finger. The adhesive band 1 is placed on the finger 2 where the contact points 4 will come in contact with the tongue whenever the fingers are inserted into the mouth. The electrodes 3 connect the electrode contact points 4 to an external power supply 5. The external power supply 5 is sufficient to supply enough electrical current to produce the desired effect yet not harm the individual. The power supply 5 may be affixed to the individual's arm or the back of the individual's hand.

As the fingers are inserted into the individual's mouth the electrode contact points 4 will come in contact with the tongue. Electric current will flow through the saliva and tissue of the tongue. Electrolytes, which are found in saliva and blood contain salts formed from various metals such as iron, potassium, sodium, magnesium, and lithium; all of which occur naturally in the body. The flow of current through the saliva and tissue, due to the electrical conductance of these electrolytes, produces an extremely unpleasant taste and uncomfortable sensation, thus discouraging the individual from finger sucking.

Figure 3:
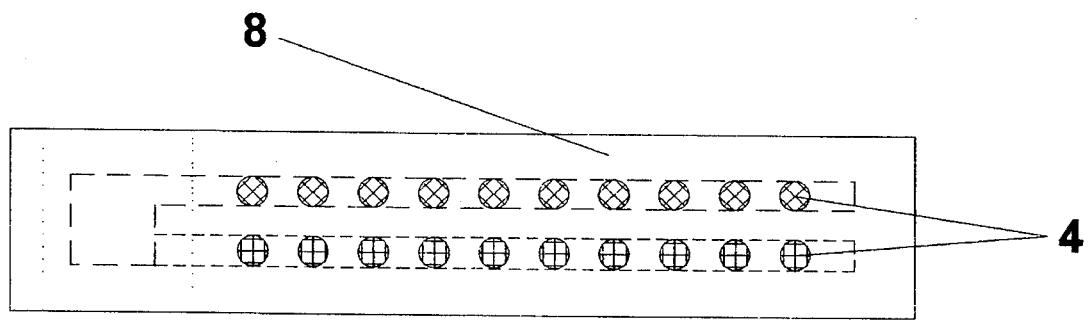
FIG. 3 is a top elevation view of the device in which the self contained voltage source method is employed.
Figure 4:
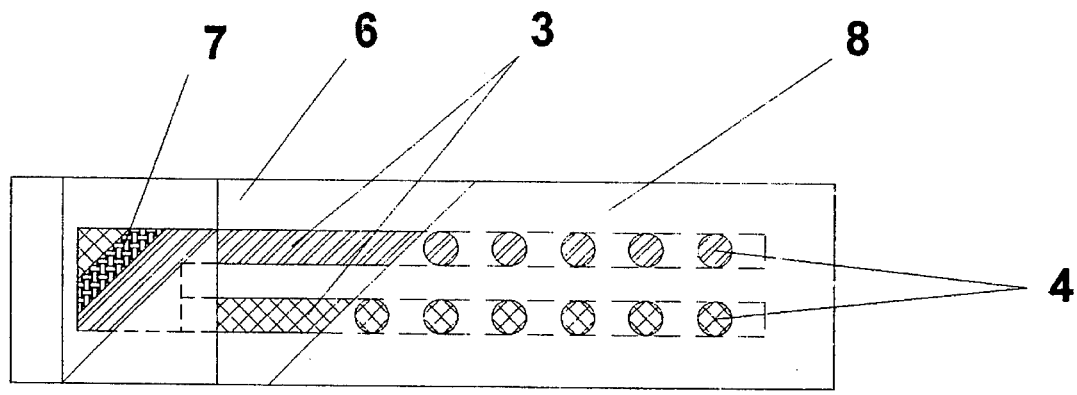
FIG. 4 is a cut away view of the device with the serf contained voltage source showing the internal construction of the combination battery-adhesive strip.

Referring to FIGS. 3 and 4, the adhesive band has been constructed with an internal battery that is complete with its own electrolyte. Two electrodes 3 are affixed onto a backing 6. These electrodes are constructed from two dissimilar metals having different electrode potentials such as silver and magnesium, or gold and aluminium, and are separated in an area by an electrolyte saturated permeable membrane 7. The membrane 7 may be saturated with an appropriate non-toxic electrolyte such as lemon juice. An electrode mask 8 is layered over the electrodes. Perforations are suitably located on the electrode mask so as to create electrode contact points 4 that will come in contact with the tongue. The electrodes 3, being of dissimilar metals having differing electrode potentials and being separate by an electrolyte saturated permeable membrane, create a battery. The tongue tissues provide the external resistive circuit through which the current flows.

Figure 5:
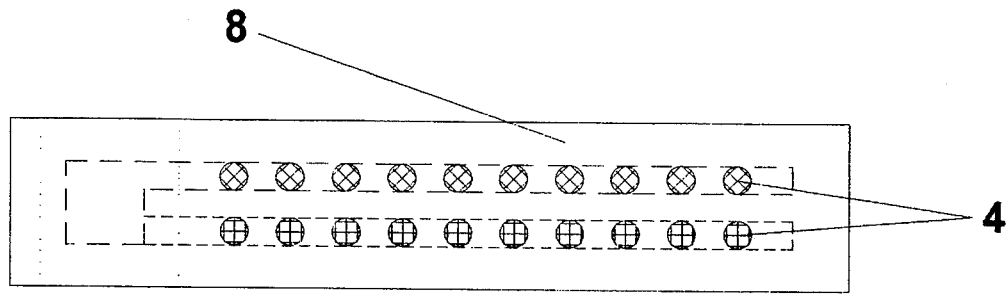
FIG. 5 is a top elevation view of the device in which the dissimilar metals combine with the electrolytes present in the child's saliva to form a voltage source.
Figure 6:
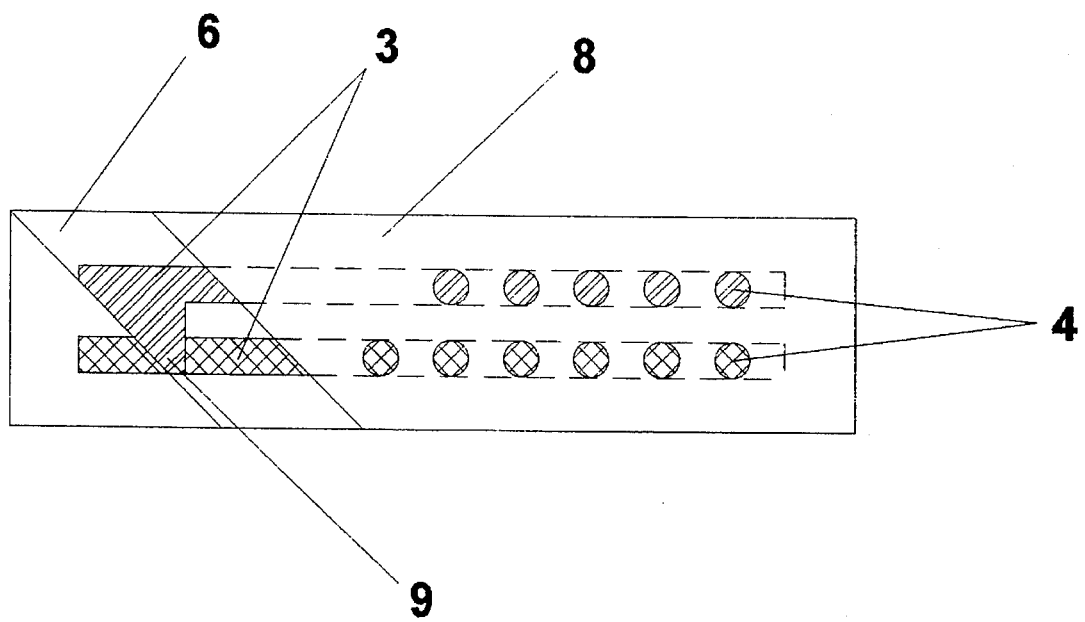
FIG. 6 is a cut away view of the device with the dissimilar metal electrodes showing the internal construction.

Referring to FIGS. 5 and 6, it can be seen that an adhesive band has been so constructed as to produce and deliver its own electrical charge. The electrodes 3 are affixed onto a backing 6. As with the previously described adhesive band, these electrodes are of dissimilar metals having differing electrode potentials such as silver and magnesium, or gold and aluminium. These electrodes 3 are joined at a point 9 in such a manner so as to provide an electrical path, and rely on the individual's saliva to provide sufficient electrolyte for current flow. An electrode mask 8 is layered over the electrodes. Perforations in the electrode mask 8 are suitably located so as to create electrode contact points 4 that come into contact with the tongue. The electrical contact point 9 provides an extremely low resistance circuit, while the saliva and electrodes 3 being made from dissimilar metals having different electrode potentials, create a battery. As in the previously described designs, a slight current would flow through the tissues of and saliva on the individual's tongue producing an unpleasant yet harmless taste and sensation.

I claim:

1. An apparatus for discouraging finger sucking by delivering a small electrical current through an individual's tongue tissues, said individual's tongue being coated with saliva, said electrical current having the effect of producing an unpleasant sensation and taste, said apparatus comprising a multi-layered adhesive band, said band further comprising a backing layer, an electrode membrane layer, and an electrode mask layer, said electrode membrane layer further comprising two strips of dissimilar metals, said strips comprising electrodes, and a section of permeable material separating said strips of dissimilar metals, said permeable material being saturated with electrolyte and separating said electrodes, said electrode membrane being sandwiched between said backing layer and said electrode mask layer, said electrode membrane further comprising two electrode strips, said electrode strips being comprised of two dissimilar metals having different electrode potentials, said electrode strips being sandwiched between said electrode mask layer and said electrode membrane layer, said electrode strips being positioned parallel to each other with a degree of space between said electrode strips, said permeable membrane layer being saturated with an electrolyte so as to produce a small voltage between said electrode strips, said electrode mask layer further comprising a plurality of perforations, said perforations being arranged in two rows, one of said rows being located over one of said electrode strips, and the remaining said row being located over the other said electrode strip, so that portions of each said electrode strip are exposed through said electrode mask layer in order to come in contact with said individual's tongue, said backing layer having an inner and outer side, said inner side being faced toward said electrode membrane layer, and said outer side further comprising an adhesive coating so that said adhesive band may be affixed to said individual's finger by wrapping said band around said finger, said adhesive layer contacting said finger so as to expose portions of said electrode strips, through said electrode mask layer, toward said individual's tongue.

2. An apparatus as recited in claim 1, wherein said electrodes are electrically joined at a point and in contact with said saliva thus utilizing said saliva as said electrolyte.

3. An apparatus as recited in claim 1, wherein said electrolyte comprises lemon juice.

4. An apparatus as recited in claim 1, wherein said dissimilar metals comprise silver and magnesium.

5. An apparatus as recited in claim 1, wherein said dissimilar metals comprise gold and aluminum.

* * * * *